United States Patent
Cai et al.

(10) Patent No.: US 7,527,771 B1
(45) Date of Patent: May 5, 2009

(54) DISSOLVING METAL PARTICLES FROM SUPPORTED CATALYST USING ULTRASONIC ENERGY, SOLVENT AND ETCHANT

(75) Inventors: Juan Cai, Fremont, CA (US); Mats Larsson, Sunnyvale, CA (US); Jifei Jia, Mountain View, CA (US); Xianghong Hao, Sunnyvale, CA (US); Jian Wang, San Mateo, CA (US)

(73) Assignee: Nanostellar, Inc., Redwood City, CA (US)

( * ) Notice: Subject to any disclaimer, the term of this patent is extended or adjusted under 35 U.S.C. 154(b) by 766 days.

(21) Appl. No.: 11/016,578

(22) Filed: Dec. 17, 2004

(51) Int. Cl.
*C01B 19/00* (2006.01)

(52) U.S. Cl. .......................... 423/1; 423/22; 423/658.5; 502/24; 502/334; 502/439; 75/743; 75/744

(58) Field of Classification Search .............. 423/1, 423/22, 658.5; 502/24, 334, 439; 134/1; 75/743, 744
See application file for complete search history.

(56) References Cited

U.S. PATENT DOCUMENTS 4,295,996 A * 10/1981 Bearden et al. ............ 502/183
4,992,614 A * 2/1991 Rodewald ................... 585/722
5,866,495 A * 2/1999 Fung et al. .................. 502/37
7,128,840 B2 * 10/2006 Wai et al. ................... 210/634

OTHER PUBLICATIONS

Flynn, et al., J. Catal. 33, 233-48, 1974, no month.*
Jung Whan Yoo et al., "Characterization of Pt Nanoparticles Encapsulated in $Al_2O_3$ and Their Catalytic Efficiency in Propene Hydrogenation," *J. Phys. Chem. A*, 2002, vol. 106: pp. 2049-2054.
Zhong L. Wang et al., "Shape Transformation and Surface Melting of Cubic and Tetrahedral Platinum Nanocrystals," *The Journal of Physical Chemistry B*, Aug. 1998, vol. 102(32): pp. 6145-6151.

* cited by examiner

*Primary Examiner*—Steven Bos
(74) *Attorney, Agent, or Firm*—Patterson & Sheridan, LLP (57) ABSTRACT

A sample preparation method for characterization of nanoparticles embedded in the supports of heterogeneous catalysts, with improved particle dispersion, is introduced. The supported catalyst is first ground or milled into fine powder. Then, the powder is mixed into an organic solvent, and an etchant is added to the solvent to digest the supports and release metallic nanoparticles. The resulting solution is then placed in an ultrasonic bath where ultrasonic waves are generated and applied to the solution. The ultrasonic waves suppress agglomeration of the particles and also break up those particle clusters resulting from agglomeration during the prior steps. Subsequently, a sample is extracted from the solution and prepared for analysis.

10 Claims, 6 Drawing Sheets

DISSOLVING METAL PARTICLES FROM SUPPORTED CATALYST USING ULTRASONIC ENERGY, SOLVENT AND ETCHANT

BACKGROUND OF THE INVENTION

1. Field of the Invention

The present invention generally relates to preparing samples for characterization, and more particularly to preparing samples for TEM (Transmission Electron Microscopy) from supported catalysts containing nanometer sized metal particles.

2. Description of the Related Art

As the size of metal particles used in catalysts has decreased to the nanometer level (roughly 1 to 100 nm), it has become increasingly difficult to characterize the physical properties of such metal particles. TEM is a common technique used to obtain 2-D images of nanometer sized particles, and is capable of resolving particle sizes down to the sub-nanometer level. An article by Zhong L. Wang, Janet M. Petroski, Travis C. Green, and Mostafa A. El-Sayed entitled, "Shape Transformation and Surface Melting of Cubic and Tetrahedral Platinum Nanocrystals," Journal of Physical Chemistry B, Vol. 102, pp. 6145=6151 (1998), shows a traditional TEM sample preparation method. Although this technique works fine for particles with size larger than 5 nm, in practice, it has been proved to be difficult to clearly resolve tiny particles (<2 nm) on supports, because of the noisy image background caused by the supports. As a result, physical properties of these particles are often inaccurately characterized.

Figure 1:
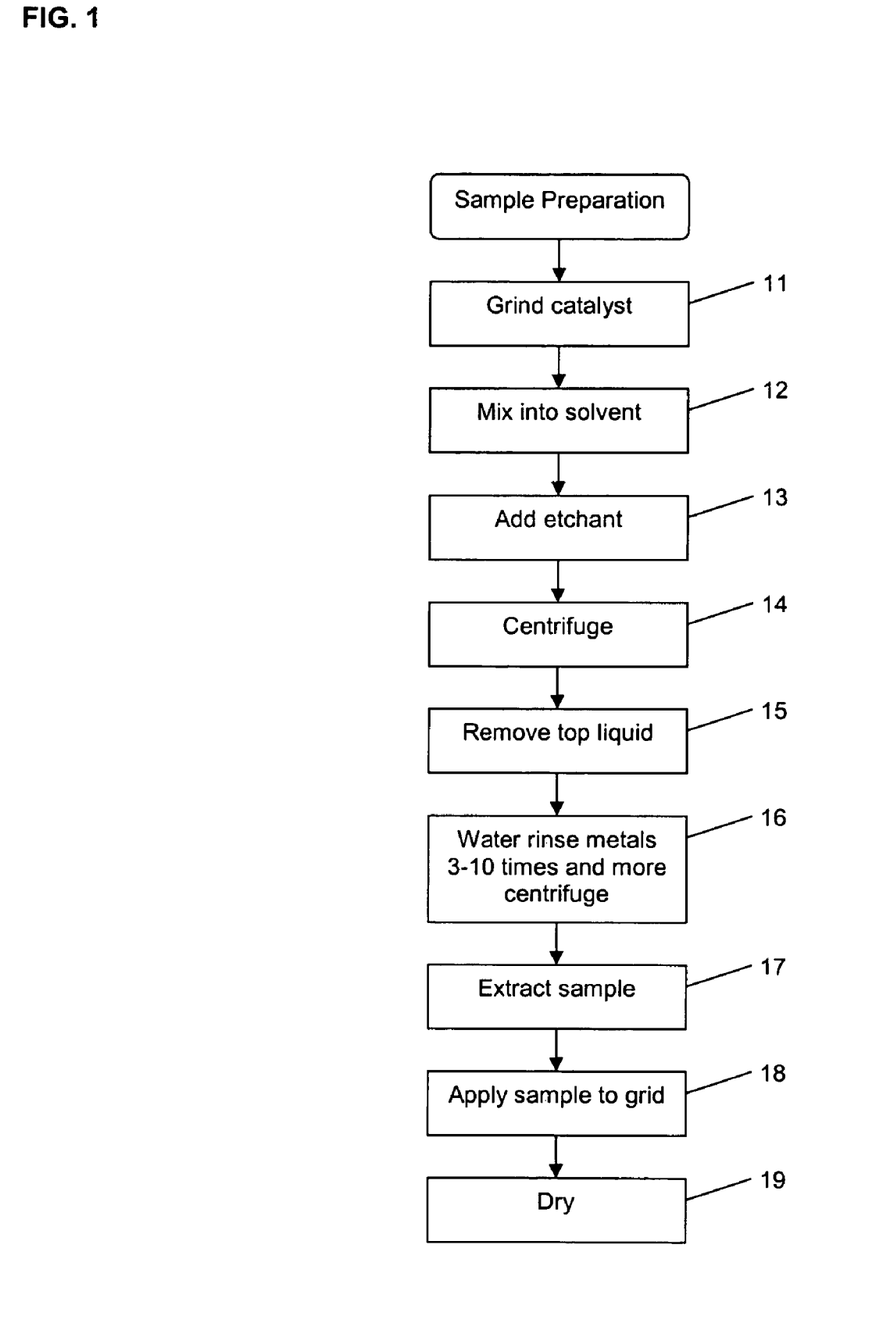
FIG. 1 is a flow diagram illustrating the process steps for preparing a characterization sample according to a prior art.

Another common technique that is used in the prior art for preparing characterization samples of supported catalysts for TEM was mentioned in an article by Jung Whan Yoo, David Hathcock, and Mostafa A. El-Sayed entitled, "Characterization of Pt Nanoparticles Encapsulated in Al2O3 and Their Catalytic Efficiency in Propene Hydrogenation," Journal of Physical Chemistry A, Vol. 106, pp. 2049-2054 (2002), and is illustrated in FIG. 1. In Step 11, the supported catalyst is ground or milled into fine powder. Then, the supported catalyst in its powder form is mixed into an organic solvent, such as acetone or ethanol (Step 12). In Step 13, an etchant is added to the solvent to digest the supports and thereby release the metal particles. The resulting solution is then placed in a centrifuge to sediment the metal particles, and then the top liquid etchant is removed. (Steps 14 and 15). Thereafter, the sediment metals are rinsed by water and centrifuged several more times (Step 16). Subsequently, a sample is extracted from the solution (Step 17) and applied to a copper grid that is used by the TEM (Step 18). Before the copper grid is placed in the TEM for imaging, the sample is dried (Step 19).

Figure 2:
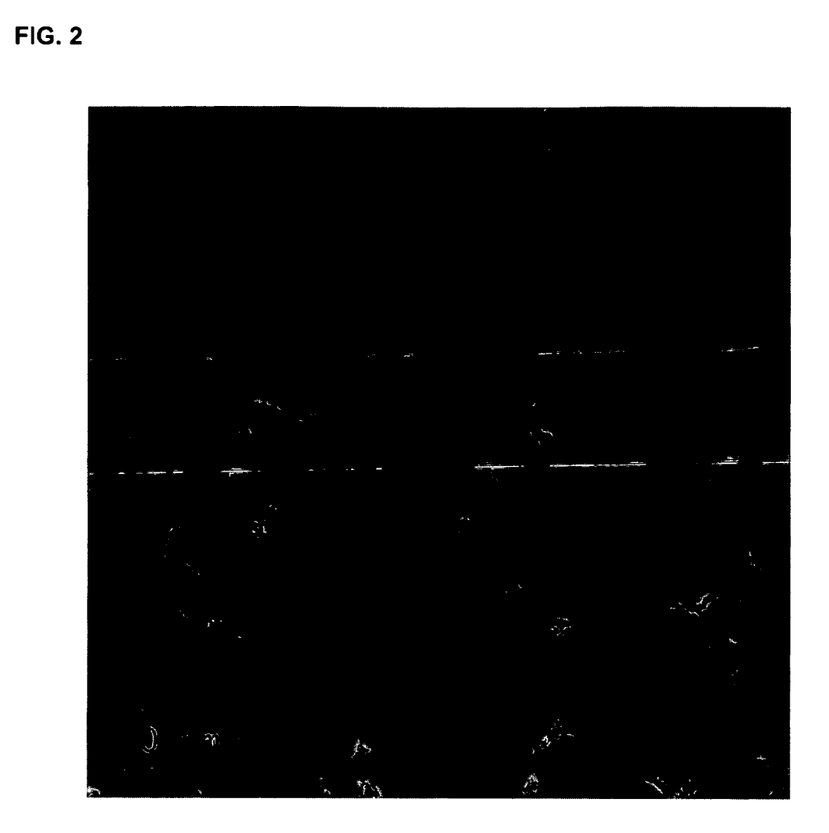
FIG. 2 is a TEM image of a characterization sample prepared according to FIG. 1.

FIG. 2 is an image obtained by the TEM from the characterization sample prepared from an alumina-supported platinum catalyst according to the process of FIG. 1. The scale for this image is shown on the image at the bottom left hand corner as 10 nm. All the particles in the image represent platinum. The different grades of shade are due to particle orientation and size. Because of the agglomeration of particles, boundaries are difficult to draw. The area data is compiled for all particles whose boundaries can be resolved in the TEM image, and the diameters of the particles are derived from the area data using conventional techniques. Usually, several TEM images are taken from one sample, and the total number of analyzed particles is counted.

Figure 3:
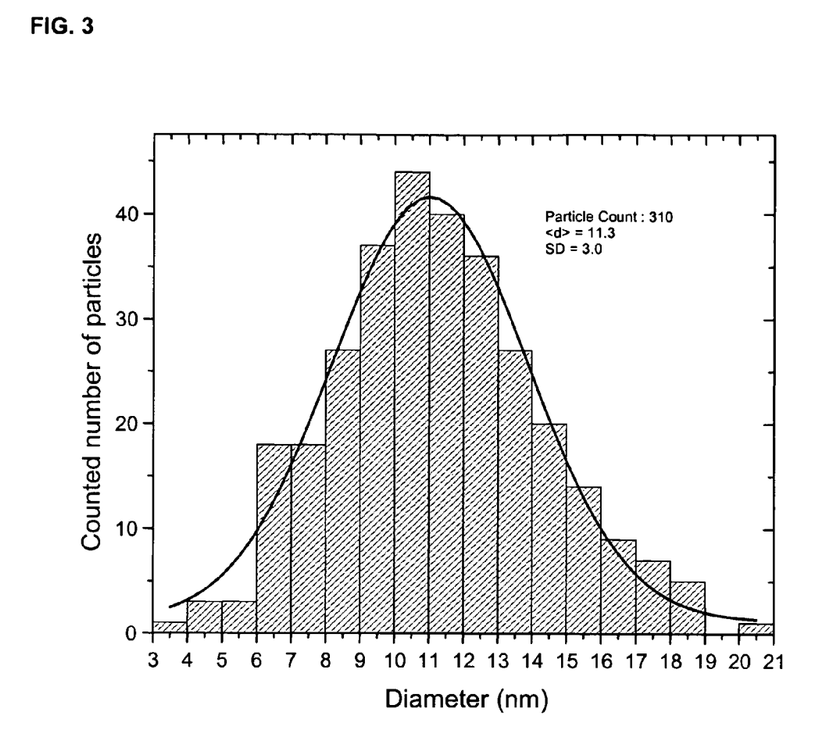
FIG. 3 is a graph showing the size distribution of metal nanoparticles that are contained in the characterization sample prepared according to FIG. 1.

FIG. 3 is a graph showing the diameter distribution of platinum particles in a characterization sample prepared from an alumina-supported platinum catalyst in accordance with the process of FIG. 1. The total number of particles was determined to be 310. The diameter range of the platinum particles was determined to be 3.8-20.6 nm and the average diameter of the platinum particles was determined to be 11.3 nm.

The accuracy of the sample prepared according to FIG. 1 could not be verified when the same alumina-supported platinum catalyst was characterized using a chemisorption (CO absorption) method, which provides for a fairly accurate measure of the average diameter. Using the chemisorption method, the average diameter of the platinum particles was determined to be 2.8 nm, more than 8 nm smaller than the average diameter determined from the sample prepared according to FIG. 1. It is obvious that sample preparation following the process of FIG. 1 has the following drawbacks: a) small particles may not sediment during centrifuge, and they may be lost in the rinse process; and b) particles agglomerate together. As a result, small particles may be overlooked during image analysis.

SUMMARY OF THE INVENTION

An object of the present invention is to provide a method for preparing a characterization sample used for TEM or other similar methods like SEM (Scanning Electron Microscopy), STEM (Scanning Transmission Electron Microscopy) or XRD (X-ray Diffraction). In comparison to the methods mentioned previously, the present invention provides more distinctive images of individual nanoparticles.

According to an embodiment of the invention, the material being characterized, e.g., an alumina-supported catalyst having nanometer sized platinum particles embedded within pores of the alumina support, is ground or milled into fine powder. Then, the powder is mixed into an organic solvent (such as acetone or ethanol), and an etchant is added to the solvent. When the alumina-supported catalyst is the material being characterized, the etchant that is added is hydrofluoric (HF) acid. The HF acid is effective in etching alumina and causes a release of the supported metal particles from the alumina support. The desired concentration of HF in the resulting solution is about 20-25%, although HF concentration in the range of 10-50% will also work. The resulting solution is then ultrasonificated for 1 hr. The ultrasonic waves suppress agglomeration of the particles and also break up those particle clusters resulting from agglomeration during the sampling process. The etching process must last for at least 12 hrs. Subsequently, a sample is extracted from the solution and applied to a metal grid, preferably a molybdenum grid, which is used in TEM characterization. Before the metal grid is placed in the TEM for imaging, the sample is dried.

The characterization samples prepared according to the invention are more representative than the characterization samples prepared according to the prior art. For example, the average diameter of platinum particles that are part of an alumina-supported catalyst was determined to be 2.5 nm from the TEM image of the characterization sample prepared according to the invention. This compares well with the average diameter of 2.8 nm determined using the chemisorption method and represents a 400% improvement over the prior art.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

The TEM sample preparation method according to the invention may be practiced with various metal-support combinations. For example, the metal may consist any of the following: Pt, Pd, Ru, Rh, Re, Ir, Os, Fe, Co, Ni, Cu, Ag, Au, Zn, Cd, In, Ga, Sn, Pb, Bi, Sb, Ti, Zr, Cr, Mo, W, V, Nb and Mn. When HF acid is used as an etchant, any of Pt, Pd, Ru, Rh, Re, Ir, Os, Fe, Co, Ni, Cu, Ag, Au, Zn, Cd, In, Bi, Sb, Cr, Mo, and V may be used. The support material may consist any of the following: alumina, silica, oxides of vanadium, oxides of titanium, oxides of zirconium, oxides of iron, oxide of lanthanum, cerium oxides, carbon, zeolites and molecular sieves.

Figure 4:
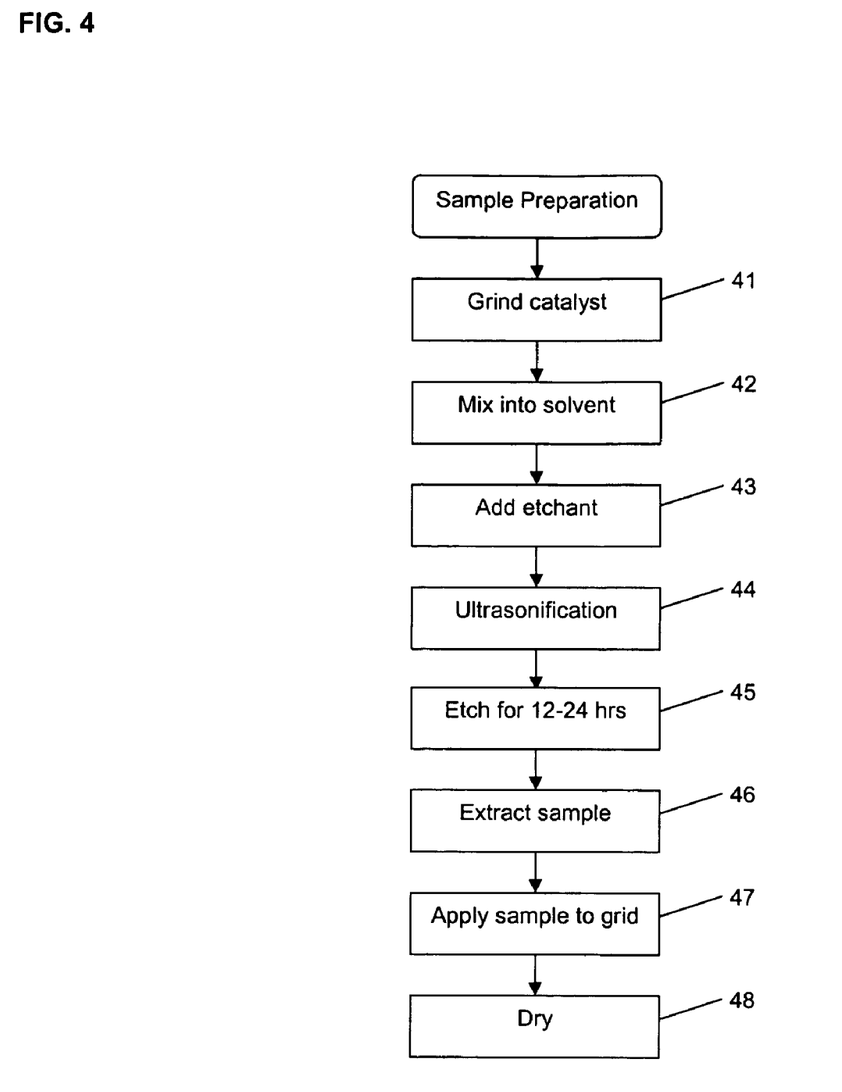
FIG. 4 is a flow diagram illustrating the process steps for preparing a characterization sample according to an embodiment of the invention.

The TEM sample preparation method according to an embodiment of the invention is illustrated in FIG. 4. In Step 41, the material being characterized, e.g., an alumina-supported catalyst having nanometer sized platinum particles embedded within pores of the alumina support, is ground or milled into fine powder using a mortar.

In Step 42, the powder is mixed into a solvent. In the example, 5-10 mg of powder is mixed in with 1-2 ml of the solvent contained in a small tube. Ethanol is the preferred solvent for alumina-supported platinum catalysts, but acetone and other alcohols may be used as the solvent.

After the powder is mixed into the solvent, 1-2 ml of an etchant is added to the tube (Step 43). When the material being characterized is alumina-supported catalyst, the etchant that is added to the solvent is hydrofluoric (HF) acid. The HF acid is effective in etching alumina and releasing the metal particles from the support. The desired concentration of HF in the tube is about 20-25%, although an HF concentration in the range of 10-50% will also work. The selection of the etchant will be different for other metal-support combinations. The etchant that is effective in etching the support but not the metal would be selected.

In Step 44, the tube is placed in an ultrasonic bath, and ultrasonic waves are applied to the solution in the tube through the ultrasonic bath for about 1 hour. The ultrasonic device used during this step may be an ultrasonic cleaner available from Branson Ultrasonic Corp. The ultrasonic waves suppress agglomeration of the particles and also break up those particle clusters resulting from agglomeration during the prior steps.

The tube is removed from the ultrasonic bath and allowed to sit for 12-24 hours during which time the HF acid etches the support and metal particles are released from the support (Step 45). Then, one drop (0.05-0.1 ml) of the solution is extracted from the tube using a pipet (Step 46), and applied to a metal grid covered with a thin (~3 nm) amorphous carbon film, preferably a molybdenum grid (Step 47). When HF acid is used as the etchant, the molybdenum grid is preferred over the copper grid that is used in the prior art sampling method, because HF tends to be more reactive with the copper grid than the molybdenum grid. The molybdenum grid may be a 400-mesh molybdenum (Mo-400CN) grid manufactured by Pacific Grid-Tech.

In Step 48, the sample volume of the solution that is applied to the metal grid is exposed to dry air within a fume hood to minimize the dust contamination from the air. Other drying methods may be employed. After drying, the metal grid is placed into the TEM for imaging.

Figure 5:
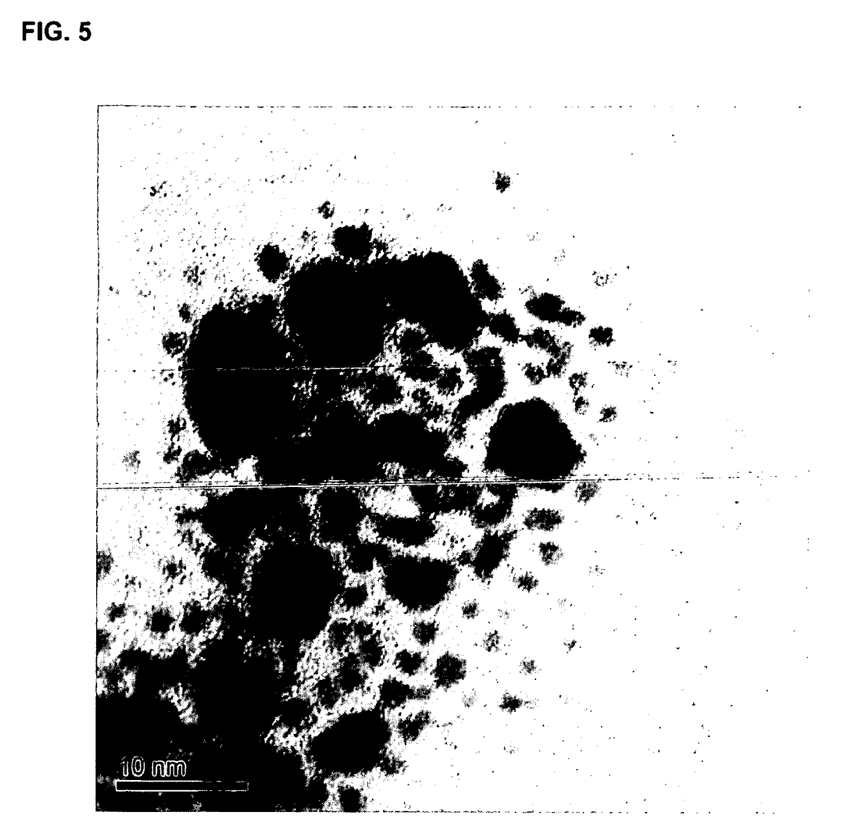
FIG. 5 is a TEM image of a characterization sample prepared according to FIG. 4.

FIG. 5 is an image obtained by the TEM device from the characterization sample prepared from an alumina-supported platinum catalyst according to the process of FIG. 4. The scale for this image is shown on the image at the bottom left hand corner as 10 nm. All particles are platinum. The different grades of shading are due to particle orientation and size. The area data is compiled for all particles in the TEM image, and the diameters of the platinum particles are derived from the area data using conventional techniques. The total number of analyzed particles from all the TEM images is also counted. Relative to the TEM image of FIG. 2, the TEM image of FIG. 5, shows particles that are less clustered and have good separation from neighboring particles. As a result, characterization of smaller diameter particles becomes possible with this image relative to the TEM image of FIG. 2.

Figure 6:
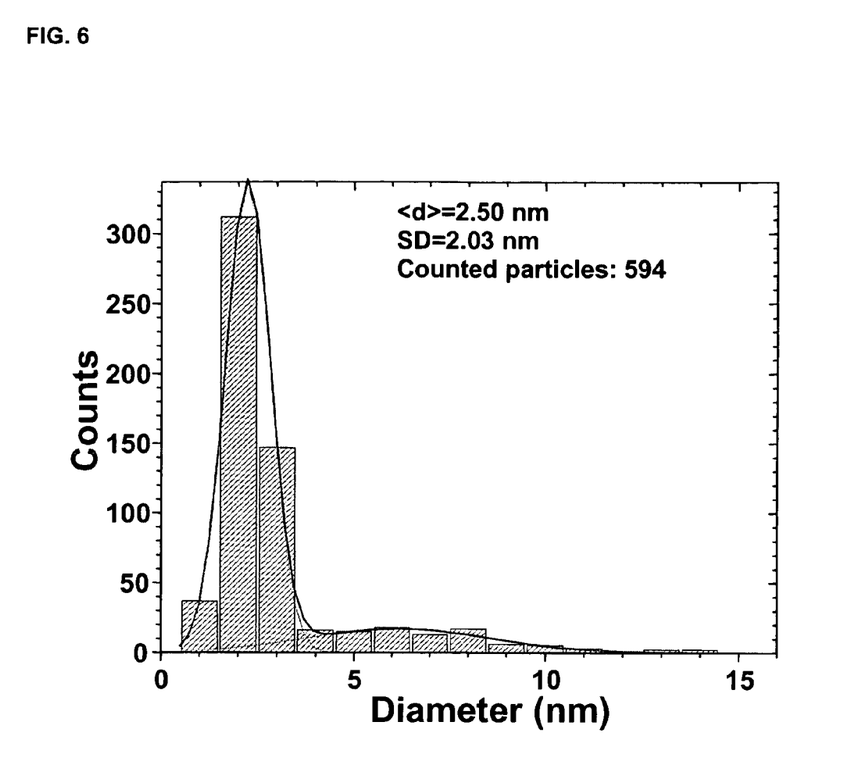
FIG. 6 is a graph showing the size distribution of metal nanoparticles in the characterization sample prepared according to FIG. 4.

FIG. 6 is a graph showing the diameter distribution of platinum particles in a characterization sample prepared from an alumina-supported platinum catalyst in accordance with the process of FIG. 4. The total number of particles was determined to be 594, almost twice as much as the total number of particles determined with the prior art sampling method. The diameter range of the platinum particles was determined to be 0.6-13.2 nm, and the average diameter of the platinum particles was determined to be 2.5 nm.

The average diameter determined with the sample prepared according to FIG. 4 was compared with the average diameter determined using a chemisorption (CO absorption) method. Using the chemisorption method, the average diameter of the platinum particles was determined to be 2.8 nm. The average diameter determined with the sample prepared according to FIG. 4 compares well with this value and is a 400% improvement from the average diameter determined with the sample prepared according to FIG. 1.

While particular embodiments according to the invention have been illustrated and described above, those skilled in the art understand that the invention can take a variety of forms and embodiments within the scope of the appended claims.

What is claimed is:

1. A method of preparing a characterization sample from a supported catalyst having metal particles dispersed throughout the support material, comprising the steps of:
  introducing the supported catalyst having metal particles into a liquid;
  adding an etchant into the liquid to separate the metal particles from its support material;
  applying ultrasonic energy to the liquid comprising the etchant and the metal particles; and
  after the step of applying, extracting a sample volume of the liquid comprising the etchant and the metal particles, wherein the ultrasonic energy is applied for about 1 hour and then stopped, and the sample volume is extracted 12 to 24 hours after stopping of the ultrasonic energy.

2. The method according to claim 1, wherein the support material comprises alumina and the etchant comprises HF acid.

3. The method according to claim 2, wherein the liquid comprising the etchant has an HF concentration of about 20-25% by weight.

4. The method according to claim 1, wherein the liquid comprises ethanol.

5. The method according to claim 1, wherein the metal particles comprise nanometer sized platinum particles.

6. The method according to claim 1, further comprising the step of grinding the supported catalyst into fine powder form prior to introducing it into the liquid.

7. A method of preparing a characterization sample from a supported catalyst having platinum metal particles dispersed throughout the support material, comprising the steps of:

introducing the supported catalyst having platinum metal particles into a liquid;

adding HF acid into the liquid to separate the platinum metal particles from its support material;

applying ultrasonic energy to the liquid comprising the HF acid and the platinum metal particles; and after the step of applying, extracting a sample volume of the liquid comprising the HF acid and the platinum metal particles wherein the ultrasonic energy is applied for about 1 hour and then stopped, and the sample volume is extracted 12 to 24 hours after stopping of the ultrasonic energy.

8. The method according to claim 7, wherein the liquid comprising the HF acid has an HF concentration of about 20-25% by weight.

9. The method according to claim 7, wherein the liquid comprises ethanol.

10. The method according to claim 7, wherein the support material comprises alumina.

* * * * *

UNITED STATES PATENT AND TRADEMARK OFFICE
CERTIFICATE OF CORRECTION

| | | |
|---|---|---|
| PATENT NO. | : 7,527,771 B1 | Page 1 of 1 |
| APPLICATION NO. | : 11/016578 | |
| DATED | : May 5, 2009 | |
| INVENTOR(S) | : Cai et al. | |

It is certified that error appears in the above-identified patent and that said Letters Patent is hereby corrected as shown below:

On the title page, item (54), and column 1, line 1, please replace the title "DISSOLVING METAL PARTICLES FROM SUPPORTED CATALYST USING ULTRASONIC ENERGY, SOLVENT AND ETCHANT" with -- METHOD OF PREPARING NANOPARTICLE SAMPLES FOR CHARACTERIZATION --

Signed and Sealed this
Sixteenth Day of August, 2011

David J. Kappos
*Director of the United States Patent and Trademark Office*